(12) United States Patent
Osborne et al.

(10) Patent No.: US 6,939,369 B2
(45) Date of Patent: Sep. 6, 2005

(54) INTRALUMINAL GRAFT ASSEMBLY AND VESSEL REPAIR SYSTEM

(75) Inventors: Thomas A. Osborne, Bloomington, IN (US); Hans A. Timmerman, Portland, OR (US)

(73) Assignee: Cook Incorporated, Bloomington, IN (US)

(*) Notice: Subject to any disclaimer, the term of this patent is extended or adjusted under 35 U.S.C. 154(b) by 589 days.

(21) Appl. No.: 10/115,146

(22) Filed: Apr. 3, 2002

(65) Prior Publication Data

US 2003/0191517 A1 Oct. 9, 2003

(51) Int. Cl.[7] ................................................. A61F 2/06
(52) U.S. Cl. .................... 623/1.11; 623/1.12; 623/1.13; 623/1.23; 606/108
(58) Field of Search ........................... 623/1.11, 1.13, 623/1.23, 1.36

(56) References Cited

U.S. PATENT DOCUMENTS

| | | |
|---|---|---|
| 3,714,671 A | 2/1973 | Edwards et al. |
| 3,983,581 A | 10/1976 | Angell et al. |
| 4,035,849 A | 7/1977 | Angell et al. |
| 4,247,292 A | 1/1981 | Angell |
| 4,388,735 A | 6/1983 | Ionescu |
| 4,470,157 A | 9/1984 | Love |
| 4,477,930 A | 10/1984 | Totten et al. |
| 4,680,031 A | 7/1987 | Alonso |
| 4,892,541 A | 1/1990 | Alonso |
| 4,902,508 A | 2/1990 | Badylak et al. |
| 5,078,726 A | 1/1992 | Kreamer |
| 5,122,154 A | 6/1992 | Rhodes |
| 5,151,105 A | 9/1992 | Kwan-Gett |
| 5,168,619 A | 12/1992 | Proto et al. |
| 5,178,618 A | 1/1993 | Kandarpa |
| 5,271,898 A | 12/1993 | Wolf et al. |
| 5,282,824 A | 2/1994 | Gianturco |
| 5,304,220 A | 4/1994 | Maginot |
| 5,336,615 A | 8/1994 | Bell et al. |
| 5,366,473 A | 11/1994 | Winston et al. |
| 5,370,691 A | 12/1994 | Samson |
| 5,387,235 A * | 2/1995 | Chuter ...................... 623/1.11 |
| 5,397,355 A | 3/1995 | Marin |
| 5,415,664 A | 5/1995 | Pinchuk |
| 5,667,523 A | 9/1997 | Bynon et al. |
| 5,782,904 A | 7/1998 | White et al. |
| 5,843,167 A | 12/1998 | Dwyer et al. |
| 6,004,347 A | 12/1999 | McNamara et al. |
| 6,071,307 A | 6/2000 | Rhee et al. |
| 6,099,558 A | 8/2000 | White et al. |
| 6,139,573 A | 10/2000 | Sogard et al. |
| 6,159,239 A | 12/2000 | Greenhalgh |
| 6,179,878 B1 | 1/2001 | Duerig et al. |
| 6,187,036 B1 | 2/2001 | Shaolian et al. |
| 6,193,745 B1 | 2/2001 | Fogarty et al. |
| 6,193,746 B1 | 2/2001 | Strecker |
| 6,200,336 B1 | 3/2001 | Pavcnik et al. |
| 6,206,911 B1 | 3/2001 | Milo |
| 6,221,102 B1 | 4/2001 | Baker et al. |
| 6,241,741 B1 | 6/2001 | Duhaylongsod et al. |
| 6,280,464 B1 | 8/2001 | Hayashi |
| 6,280,467 B1 * | 8/2001 | Leonhardt ................. 623/1.16 |
| 6,485,524 B2 * | 11/2002 | Strecker .................... 623/1.15 |

* cited by examiner

Primary Examiner—Julian W. Woo
Assistant Examiner—Sarah K. Webb
(74) Attorney, Agent, or Firm—Brinks Hofer Gilson & Lione

(57) ABSTRACT

An intraluminal graft assembly is provided. In one embodiment, the assembly comprises a support frame having first, radially smaller and second, radially larger configurations. A graft is attached to the support frame at one end by connectors and is not connected to the other end. The graft extends along only a fractional length of the support frame when in the first configuration, and substantially along the entire length of the support frame when in the second configuration. A vessel repair system is also provided. In the system, a driving member is positioned to force the support frame from the first configuration to the second configuration.

12 Claims, 8 Drawing Sheets

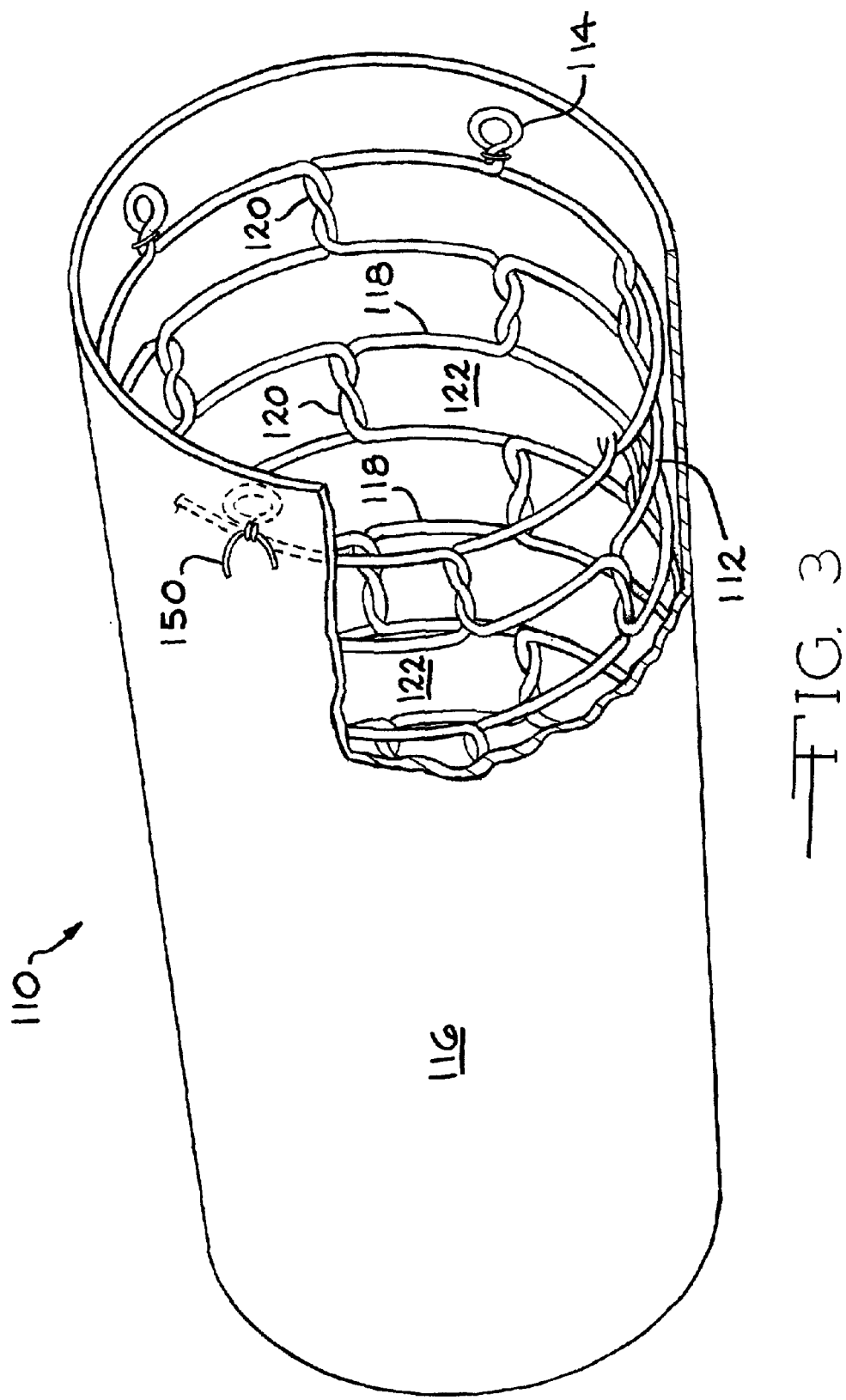

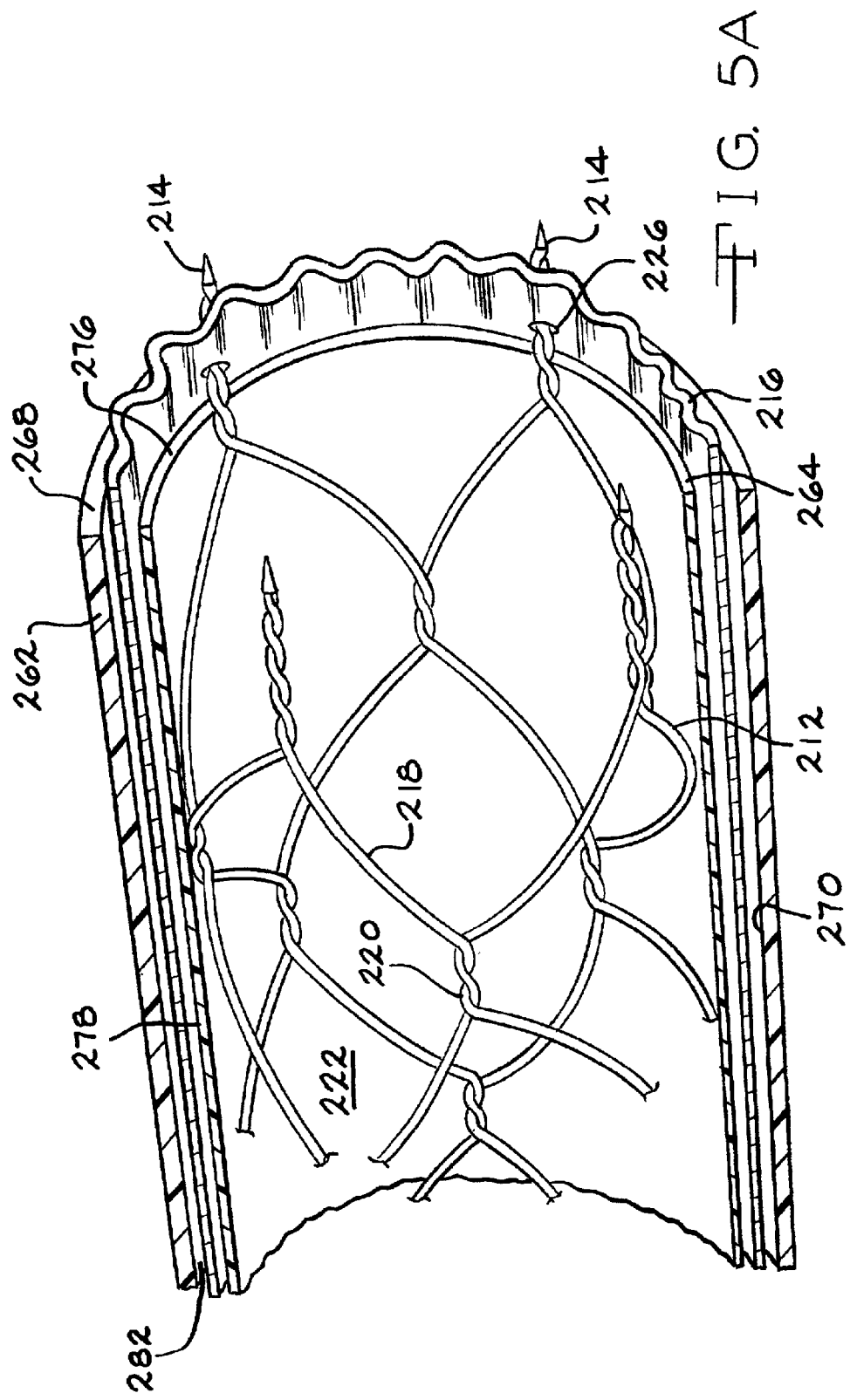

INTRALUMINAL GRAFT ASSEMBLY AND VESSEL REPAIR SYSTEM

FIELD OF THE INVENTION

The present invention relates generally to radially self-expanding support frames for intraluminal therapeutic use. More particularly, the present invention relates to an intraluminal support frame having a graft material disposed on its surface.

BACKGROUND OF THE INVENTION

Various types of disease conditions present clinical situations in which a vessel of a patient needs to be artificially supported or held in an open position. For example, blood flow through an artery can be impeded due to a build-up of cholesterol. Also, walls of a vessel may be weakened by an aneurysm.

Intraluminal support frames, sometimes referred to as stents, provide an artificial mechanism to support a body vessel. Generally, these support frames are tubular structures formed in a mesh pattern of metal, plastic, or other suitable material. Self-expanding support frames are able to take on a radially compressed configuration, which facilitates delivery of the frame to the site of interest. Once at the site, the force holding the frame in the radially compressed configuration is removed, and the frame takes on its radially expanded configuration. In this configuration, the frame exerts radially outward force on the vessel, which supports the vessel.

As indicated above, the support frame is typically made of a metal or other suitable material in a mesh-like pattern. While the mesh structure allows for the radial expansion, it concentrates the outward force exerted on the vessel to the individual threads forming the mesh. Little or no force is exerted on the vessel walls in the voids or empty spaces in the mesh structure. As a result, tissue ingrowth can occur in the voids, which may lead to restenosis of the vessel and may necessitate additional treatment for the patient, which might include replacement of the stent.

Several devices have been proposed that combine a graft material with a support frame. The use of a graft provides a continuous surface for supporting the vessel and operates to minimize the ingrowth problem mentioned above.

When compressed, a typical support frame often has a greater length than when it is in its radially expanded configuration. This, in the past, has forced the use of graft materials that can change dimensions along with the support frame. As a result, grafts made of woven and other elastic materials populate the prior art. This placed constraints on the types of graft material that could be utilized. Furthermore, the stretching of the graft material presents an opportunity for kinking, overstretching, and even tearing of the graft.

In view of these and other deficiencies of the prior art, there is a need for an intraluminal graft assembly that allows the support frame to radially expand independently of the graft material.

SUMMARY OF THE INVENTION

The present invention provides an intraluminal graft assembly that includes a radially self-expanding support frame of a tubular shape and a graft disposed on the frame. One or more connectors are disposed on a first end of the support frame and attach the graft to the frame. The graft is free from, i.e., not connected to, the second end of the support frame.

The graft extends along a fractional length of the length of the support frame when the frame is in its radially compressed configuration. This allows the graft to extend substantially along the entire length of the support frame when the frame is in its shorter, radially expanded configuration.

The connectors can take various forms. Preferably, the connectors comprise a barb or loop structure formed from a thread of the frame. The connector can pass through an opening in the graft, or can otherwise be attached to the graft, such as by sutures.

In one embodiment, the graft assembly comprises a radially selfexpanding support frame comprising a tubular structure formed of one or more frame threads and having a first end, a second end, a radially compressed configuration with a first length and a first diameter, and a radially expanded configuration with a second length that is shorter than the first length and a second diameter that is larger than the first diameter; at least one connector on the first end of the support frame; and a graft disposed on the support frame and attached to the first end by the connector. The graft extends along a fractional length of the first length of the support frame when the frame is in the radially compressed configuration. Also, the graft is free of the second end of the support frame.

The present invention also provides a system for repairing a vessel of a patient. In one embodiment, the system comprises a graft assembly according to the present invention and a deployment device that includes first and second coaxial sleeves. The second sleeve is disposed within an interior lumen of the first sleeve, creating an annular space between the sleeves. The support frame is substantially disposed in an interior lumen of the second sleeve and the graft is substantially disposed in the annular space between the first and second sleeves. The first end of the support frame, which is attached to the graft via one or more connectors, extends beyond the first and second sleeves. A driving member is disposed in the lumen of the second sleeve.

The present invention also provides a method of placing a graft on a support frame. One embodiment according to the invention comprises providing a system for repairing a vessel of a patient according to the invention and manipulating the driving member of the system such that the driving member forces the support frame out of the lumen of the second sleeve, and the graft out of the annular space. While exiting the second sleeve at the repair site, the support frame adopts its radially expanded configuration.

The invention is defined in the appended claims. Additional understanding of the invention can be achieved by reference to the following figures and detailed description of preferred embodiments of the invention.

BRIEF DESCRIPTION OF THE DRAWINGS

FIG. 3 is a perspective view, partially broken away, of an intraluminal graft assembly according to a second preferred embodiment of the present invention. The support frame of the assembly is in a radially expanded configuration.

FIG. 5A is a magnified view of the distal end of the repair system illustrated in FIG. 4.

DETAILED DESCRIPTION OF THE PREFERRED EMBODIMENTS OF THE INVENTION

The following description of preferred embodiments of the invention provides examples of the present invention. The embodiments discussed herein are merely exemplary in nature, and are not intended to limit the scope of the invention in any manner. Rather, the description of these preferred embodiments serves to enable a person of ordinary skill in the relevant art to make and use the present invention.

Figure 1:
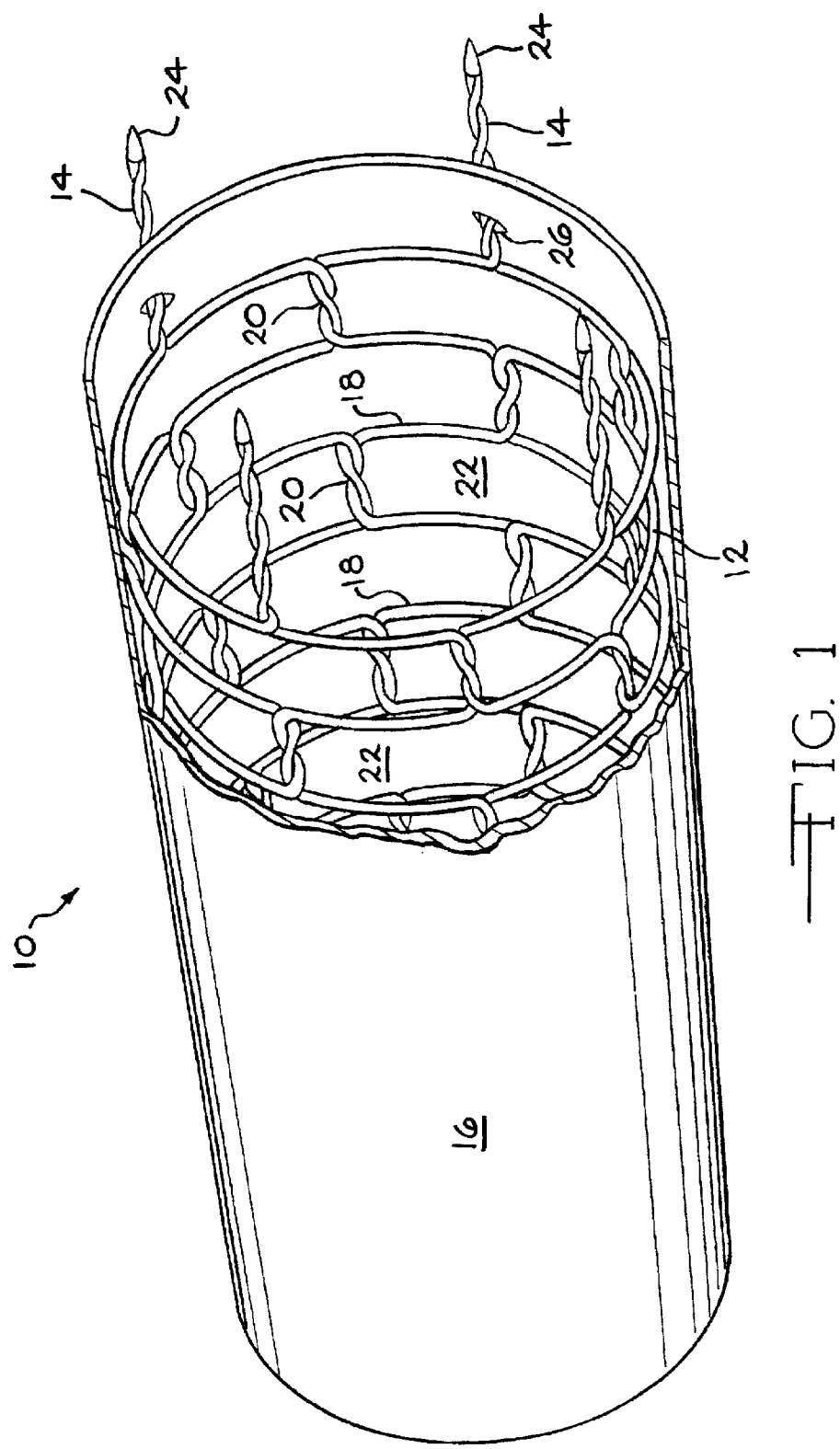
FIG. 1 is a perspective view, partially broken away, of an intraluminal graft assembly according to a first preferred embodiment of the present invention. The support frame of the assembly is in a radially expanded configuration.

FIG. 1 illustrates an intraluminal graft assembly 10 according to a preferred embodiment of the invention. The graft assembly 10 includes a support frame 12, one or more connectors 14, and a graft 16.

Figure 2:
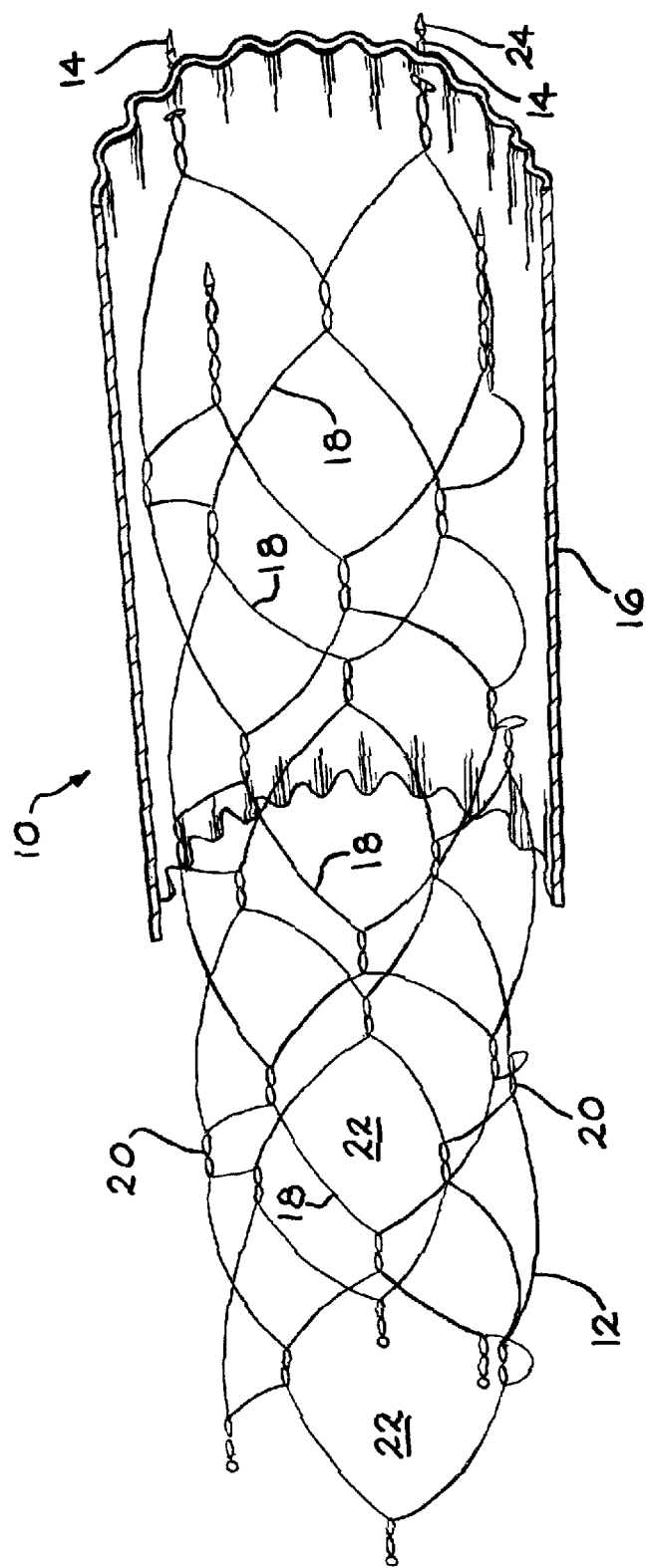
FIG. 2 is a partial cross-sectional view of the assembly of FIG. 1. The support frame of the assembly is in a radially compressed configuration.

A variety of stent types can be used as the support frame. For example, both self-expanding and balloon-expandable stents can be used. Preferably, the support frame 12 is a radially self-expanding support frame formed into a tubular structure. The support frame 12 is able to take on at least two configurations: a radially compressed configuration and a radially expanded configuration. FIG. 1 illustrates the support frame 12 in the radially expanded configuration. The support frame 12 takes on the radially compressed configuration when a constraining force is applied around the frame 12, such as when the frame is stored in a delivery device for later deployment. FIG. 2 illustrates the graft assembly 10 of FIG. 1 with the support frame 12 in the radially compressed configuration. In this configuration, the support frame 12 has a diameter that is smaller than the diameter of the frame 12 when in the radially expanded configuration (illustrated in FIG. 1). Also, the support frame 12 has a length that is greater than the length of the frame 12 when it is in the radially expanded configuration (illustrated in FIG. 1).

The support frame 12 is formed of one or more frame threads 18. As the support frame can be formed from a variety of materials and methods, the threads can have various configurations. For example, the threads can comprise wires or material left in a form after an etching or cutting process. As illustrated in FIG. 1, the threads 18 are preferably wire-like structures formed of the material chosen for the support frame 12. The threads 18 are repeatedly wound together (or upon itself if a single thread is chosen) to form a plurality of intersections 20 and open cells 22. Preferably, as best illustrated in FIG. 1, the intersections 20 comprise simple weave overlaps between threads or portions thereof. Because of the overlap structure, the support frame 12 remains flexible by allowing the cells 22 to change in size and configuration as the frame 12 is manipulated, such as when the frame 12 changes from a radially compressed configuration to a radially expanded configuration.

The frame threads 18 can be woven together in any suitable pattern. The weaving pattern illustrated in FIG. 1 merely represents a preferred pattern for use in the present invention. A wide variety of weaving patterns are known to those skilled in the art, and any suitable pattern can be used. The pattern chosen need only allow for the use of connectors 14 to attach the graft 16 to the frame 12, as described below. Examples of other suitable patterns include simple three thread tubular braids (two-dimensional braid) and a three-dimensional braid. The support frame 12 can be fabricated from the frame threads 18 by using various industrial weaving techniques known in the art.

The support frame 12, and therefore the frame threads 18, can be formed from a wide variety of materials. The material chosen should allow the support frame 12 to radially expand and should also be medically acceptable (e.g., biocompatible). Accordingly, the support frame 12 can be formed of a wide variety of natural and synthetic materials including collagen, various thermoplastics, and various metals. Examples of suitable thermoplastics include polyesters, polypropylenes, polyethylenes, polyurethanes, polytetrafluoroethylenes (PTFEs), and combinations and mixtures thereof. Examples of suitable metals include stainless steel, titanium, nickel-chromium alloys, and nickel-titanium alloys. Preferred materials include stainless steel and nickel-titanium alloys known to those skilled in the art.

Particularly preferred materials include materials that allow the support frame to radially self-expand, such as various shape memory materials. In this embodiment, the shape memory properties allow the frame 12 to return to a predetermined configuration when a particular temperature is encountered. Shape memory materials, such as various nickel-titanium alloys and their operation are known to those skilled in the art and will not be described in detail herein.

At least one connector 14 is disposed on a first end of the support frame 12. The connector 14 is a structural member capable of retaining the graft 16 adjacent the first end of the support frame 12. That is, the connector 14 is a structural member capable of attaching the graft 16 to the first end of the support frame 12.

The size, shape and configuration of the connector 14 can vary. The connector 14 need only be able to interact with the graft 16 in a manner that accomplishes the desired attachment between the graft 16 and the first end of the support frame 12. Preferably, the connector 14 is integrally formed by one or more frame threads 18. For example, as illustrated in FIG. 1, the connector 14 can comprise a barb formed from the terminal ends of two frame threads 18 that have been twisted together. In this embodiment, the connector preferably includes a tapered point 24 at its end. The point 24 facilitates placement of the graft 16 over the connector 14 during fabrication of the graft assembly 10. The point 24 need not be sharp enough to be able to pierce the graft 16. Rather, the point 24 need only have a pointed shape that facilitates navigation of the connector 14 through a structure, such as an aperture 26 in the graft 16.

FIG. 3 illustrates a second preferred embodiment of the graft assembly 110 of the present invention. This embodiment is identical to the first preferred embodiment, except as described below. Accordingly, reference numbers in FIG. 3 refer to similar features and/or components of the embodiment illustrated in FIG. 1, and differ from those in FIG. 1 by 100.

In this second embodiment, the connector 114 comprises a loop structure formed by a frame thread 118 and a suture 150. The suture 150 passes through the graft 116 and around a portion of the loop structure to achieve the desired attachment between the connector 114 and the graft 116.

As illustrated in both FIGS. 1 and 3, the connector 14, 114 preferably extends away from the second end of the support frame 12, 112 (i.e., the end opposite the end on which the connector 14, 114 is disposed). As will be described in more detail below, the graft assembly is pushed out of a repair system by a driving member. This arrangement of the connector 14,114 helps to assure that the graft 16, 116 moves with the frame 12, 112 when the frame 12, 112 is pushed out of a deployment device, such as that described below. Also, as illustrated in both FIGS. 1 and 3, the graft assembly preferably includes a plurality of connectors 14, 114 disposed around the circumference of the first end of the support frame 12,112.

A variety of other structures for attaching the graft to the support frame can be used as the connector. For example, the connector can be formed into a loop structure that pierces through the graft, the connector can be formed into a clip structure that frictionally engages an edge of the graft, or the connector can be formed into a rivet-like structure that fits through a hole in the graft and retains the graft adjacent the frame.

Referring to FIG. 1, the graft 16, as indicated above, is attached to the first end of the support frame by the connector 14. The graft 16 is free of the second end of the support frame 12. That is, the graft 16 is not attached to the second end of the support frame 12, even though the graft 16 lies adjacent to this end of the frame 12. This arrangement allows for partial separation of the graft 16 and support frame 12 when the assembly 10 is placed in a repair system, as will be described below.

As illustrated in FIG. 1, the graft 16 preferably extends substantially along the entire length of the support frame 12 when the frame 12 is in the radially expanded configuration. This allows the graft 16 to cover the frame threads 18, intersections 20, and open cells 22 when the graft assembly 10 is deployed within a body vessel in the radially expanded configuration. As illustrated in FIG. 2, the graft 16 extends along only a fractional length of the support frame 12 when the frame 12 is in the radially compressed state, such as when the assembly 10 is stored in a repair system for later deployment. As used herein, the term "fractional length" refers to a length along the support frame 12 that is less than the total length of the support frame 12 in the radially compressed configuration. The actual fractional length used will depend on several factors, including any or all of the length of the support frame 12 in the radially compressed configuration, the length of the support frame 12 in the radially expanded configuration, and the inner diameter of the vessel in which the assembly will be deployed, which indicates the percentage of the frame diameter of the radially expanded configuration that can be attained in that particular vessel. Accordingly, the fractional length utilized can be optimized based on these and other parameters. Examples of preferred fractional lengths include ¼, ½, and ¾ of the length of the support frame 12 when in the radially compressed configuration.

The graft can be made of any suitable graft material. Examples of suitable materials include mesh material, woven materials, such as fabric and Dacron (Dacron is a registered trademark of the E. I. DuPont DeNemours Company), and synthetics such as polypropylene. Also, natural materials such as collagen and extracellular matrix (ECM) materials can be used. A preferred graft material is small intestine submucosa (SIS), such as SIS harvested from swine. The preparation and use of SIS, in contexts other than that of the present invention, are known to those skilled in the art. Descriptions of this material and procedures for its preparation can be found in U.S. Pat. No. 4,902,508 to Badylak et al. for TISSUE GRAFT COMPOSITION, which is hereby incorporated into this disclosure in its entirety.

The graft 16 may define structural features that facilitate attachment of the graft 16 to the support frame 12 by the connectors 14. As illustrated in FIG. 1, for example, the graft 16 may define one or more apertures 26 that are able to receive a connector 14, such as a barb formed of twisted frame threads 18. The structural features can vary depending on the type and number of connectors 14 present on the support frame.

The graft assembly of the present invention is particularly well-suited for the repair of various types of vessels in patients. For example, the assembly can be used to provide artificial support to a weakened or blocked vessel. To be used in this manner, the graft assembly must be delivered to the site of interest and deployed, i.e., changed from a radially compressed configuration to a radially expanded configuration, from inside the lumen of the vessel.

Figure 4A:
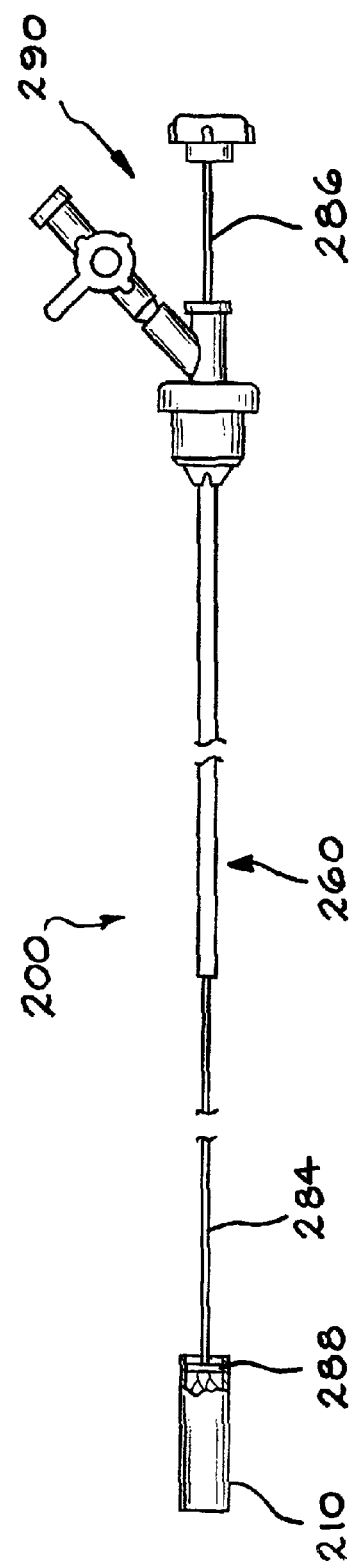
FIG. 4A is a perspective view, partially broken away, of a vessel repair system according to the present invention.
Figure 4B:
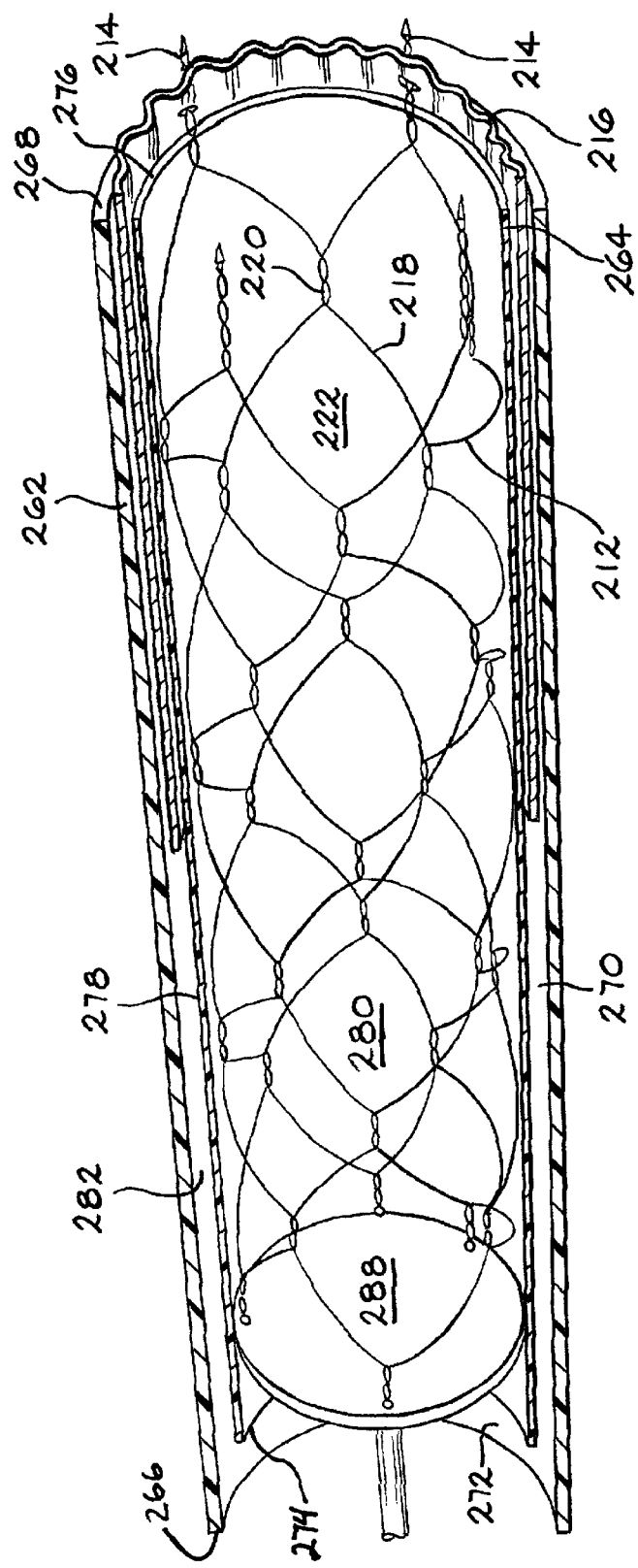
FIG. 4B is a magnified cross-sectional view of the graft assembly stored in the repair system of FIG. 4A.

FIG. 4A illustrates a preferred embodiment of a vessel repair system 200 according to the present invention. The vessel repair system incorporates a graft assembly 210 according to the present invention (detail of the graft assembly 210 is illustrated in FIG. 4B). As a result, reference numbers in FIG. 4B refer to similar features and/or components of the graft assembly as illustrated in the previous figures, but are a 200 series of numbers.

With reference to both FIGS. 4A and 4B, the vessel repair system 200 comprises a graft assembly 210, and a deployment device 260. The deployment device 260 comprises first 262 and second 264 sleeves. The first sleeve 262 has a proximal and 266, a distal end 268, and an inner surface 270 defining a first interior lumen 272. The second sleeve 264 also has a proximal end 274 and a distal end 276. The second sleeve 264 has an outer surface 278 and defines a second interior lumen 280.

The second sleeve 264 extends coaxially with the first sleeve 262 and is disposed within the first interior lumen 272 of the first sleeve 262. An annular space 282 is formed between the outer surface 278 of the second sleeve 264 and the inner surface 270 of the first sleeve 262.

The support frame 212 of the graft assembly 210 is disposed substantially within the second interior lumen 280 such that only the first end of the support frame 212 and the associated connectors 214 extend beyond the distal ends 268, 276 of the first 262 and second 264 sleeves. The graft 216 is attached to the support frame 212 by the connectors 214 as described above. The graft 216 is not connected to the second end of the support frame 212 and, as illustrated in FIG. 4B, is physically separated from the second end of the support frame 212 by the second sleeve 264.

Except for the portion that extends beyond the distal ends 268,276 of the first 262 and second 264 sleeves for attachment to the support frame 212, the graft 216 is substantially disposed in the annular space 282 between the first 262 and second 264 sleeves. When stored in the deployment device 260, the support frame 212 of the graft assembly 210 is in the radially compressed configuration. As a result, the graft 216 may not be drawn taught to the surface of the second sleeve 264. Consequently, as illustrated in FIG. 4B, the graft 216 is preferably repeatedly folded in the annular space 282 to facilitate its storage.

Figure 5B:
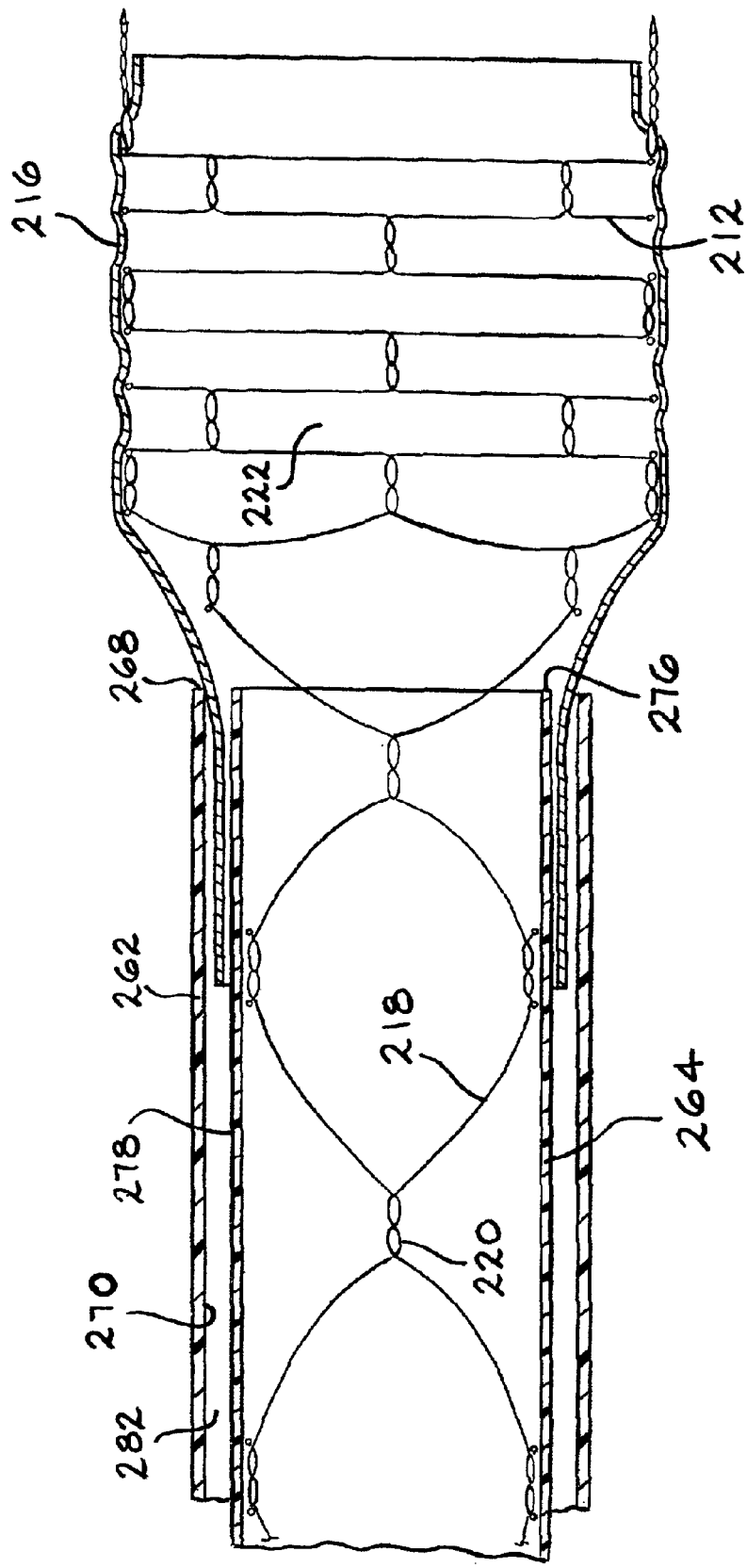
FIG. 5B is a cross-sectional view of the graft assembly of FIG. 5A in a partially expanded configuration.

The deployment device 260 also includes a driving member 284. The driving member 284 has an operating end 286 that terminates at a handle assembly 290. A driving end 288 is disposed adjacent the second end of the support frame 212 within the second sleeve 264. An operator is able to force the support frame 212 and attached graft 216 out of the deployment device 260 by pushing on the operating end 286 of the driving member 284 such that the driving end 288 forces movement of the support frame 212 relative to the first 262 and second 264 sleeves. As illustrated in FIGS. 5A and 5B, the support frame 212 takes on the radially expanded configuration as it exits the deployment device 260. As a result, the graft 216 is drawn substantially taught against the surface of the support frame 212, as best illustrated in FIG. 5B.

Thus, a preferred method of placing a graft on a support frame comprises providing a vessel repair system according to the present invention and manipulating the operating end of the driving member such that the driving end forces the support frame out of the second lumen. As the support frame exits, it pulls the graft out of the annular space. As best illustrated in FIG. 5B, the graft gradually unfolds from within the annular space and extends substantially along the entire length of the support frame as the support frame changes from the radially compressed configuration to the radially expanded configuration.

Figure 6:
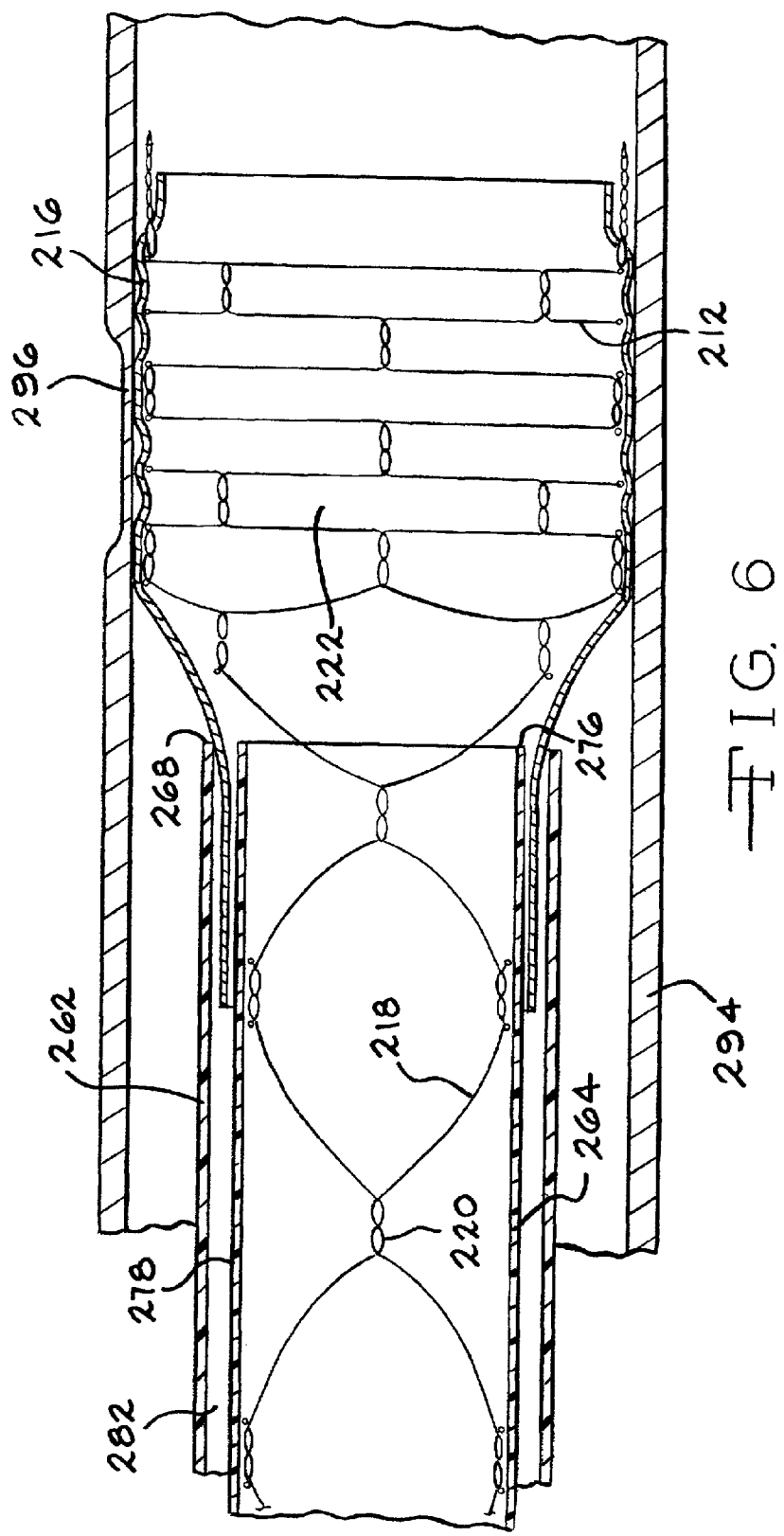
FIG. 6 is a cross-sectional view of the graft assembly partially deployed in the lumen of a vessel in a patient.

The method described above is particularly well-suited for placing the graft assembly at a point in the vessel that is in need of artificial support. FIG. 6 illustrates a schematic of this process, in which an operator inserts the distal ends 268,276 of the first 262 and second 264 sleeves into the lumen of a vessel 294 of a patient and moves these ends 266,274 to a point 296 in the vessel 294 that is in need of the artificial support. Techniques for inserting a deployment device into a vessel of a patient and navigating the device to the site of interest are known to those skilled in the art and will not be described in detail herein. The support frame 212 is forced out of the deployment device 260 as described above. The frame 212 expands and places the graft 216 at the weakened point 296 of the vessel 294. The graft 216 is secured in this position by an outward force from the frame 212.

The foregoing disclosure is the best mode devised by the inventor for practicing the invention. It is apparent, however, that several variations in intraluminal graft assemblies in accordance with the present invention may be conceivable by one skilled in the art. Inasmuch as the foregoing disclosure is intended to enable one skilled in the pertinent art to practice the instant invention, it should not be construed to be limited thereby, but should be construed to include such aforementioned variations. As such, the present invention should be limited only by the spirit and scope of the following claims.

We claim:

1. A system for repairing a vessel of a patient, said system comprising:
   a deployment device comprising
      a first sleeve having a proximal end, a distal end, and an inner surface defining a first lumen;
      a second sleeve extending coaxially with the first sleeve and having a proximal end, a distal end, an outer surface and defining a second lumen, the second sleeve disposed in the first lumen to form an annular space between the inner surface of the first sleeve and the outer surface of the second sleeve; and
      a driving member disposed in the second lumen;
   a support frame comprising a tubular structure having a length, a distal end, a proximal end, and at least one connector on the distal end, the support frame substantially disposed in the second lumen such that the connector extends beyond the distal ends of the first and second sleeves; and
   a graft attached to the connector and disposed substantially in the annular space.

2. The system of claim 1, wherein the support frame is in a radially compressed configuration and wherein the graft extends only along a fractional length of the length of the support frame.

3. The system of claim 1, wherein the connector extends in a direction away from the proximal end of the support frame.

4. The system of claim 1, wherein the graft has a thickness and defines an opening through the thickness, and wherein the connector passes through the opening.

5. The system of claim 4, wherein the support frame is formed of at least two frame threads having terminal ends; and
   wherein the connector comprises a barb formed of the terminal ends of two frame threads twisted together.

6. The system of claim 5, wherein the connector includes a tapered point.

7. The system of claim 5, wherein the connector extends in a direction away from the proximal end of the support frame.

8. The system of claim 1, wherein the connector comprises a suture passed through the graft and around a portion of the support frame.

9. The system of claim 1, wherein the graft is folded within the annular space.

10. A method of deploying a graft in a vessel, said method comprising:
    providing a system comprising
       a first sleeve having a proximal end, a distal end, and an inner surface defining a first lumen;
       a second sleeve extending coaxially with the first sleeve and having a proximal end, a distal end, an outer surface, and defining a second lumen, the second sleeve disposed in the first lumen to form an annular space between the inner surface of the first sleeve and the outer surface of the second sleeve; and
       a driving member disposed in the second lumen and having a driving end and an operating end near the proximal end of the first sleeve;
       a support frame comprising a tubular structure having a length, a distal end, a proximal end, and at least one connector on the distal end, the support frame substantially disposed in the second lumen such that the connector extends beyond the distal ends of the first and second sleeves; and
       a graft attached to the distal end of the support frame by the connector and not connected to the proximal end of the support frame, the graft being disposed substantially in the annular space; and
    manipulating the operating end of the driving member such that the driving end forces the support frame out of the second lumen and the graft out of the annular space.

11. The method of claim 10, wherein the support frame has a first configuration with a first diameter and a second configuration with a second larger diameter;
    wherein the support frame changes to the second configuration as it exits the second lumen;
    wherein the graft extends only along a fractional length of the length of the support frame when in the first configuration; and
    further comprising allowing the graft to extend substantially along the entire length of the support frame as the support frame changes from the first configuration to the second configuration.

12. The method of claim 10, further comprising inserting the proximal ends of the first and second sleeves into said vessel and navigating the proximal ends of the first and second sleeves to a point in said vessel that is in need of artificial support.

* * * * *